United States Patent [19]
Brendel et al.

[11] Patent Number: 5,856,338
[45] Date of Patent: Jan. 5, 1999

[54] SULFONAMIDE-SUBSTITUTED COMPOUNDS, PROCESSES FOR THEIR PREPARATION, THEIR USE AS A MEDICAMENT OR DIAGNOSTIC, AND PHARMACEUTICAL PREPARATION COMPRISING THEM

[75] Inventors: Joachim Brendel, Bad Vilbel; Hans Jochen Lang, Hofheim; Uwe Gerlach, Hattersheim; Klaus Weidmann, Kronberg, all of Germany

[73] Assignee: Hoechst Aktiengesellschaft, Frankfurt am Main, Germany

[21] Appl. No.: 990,455

[22] Filed: Dec. 15, 1997

[30] Foreign Application Priority Data

Dec. 16, 1996 [DE] Germany .................. 196 52 213.7
Jul. 15, 1997 [DE] Germany .................. 197 30 326.9

[51] Int. Cl.$^6$ .................. A61K 31/47; C07D 215/42
[52] U.S. Cl. .................. 514/313; 546/159
[58] Field of Search .................. 546/159, 162; 514/313

[56] References Cited

U.S. PATENT DOCUMENTS

| | | | |
|---|---|---|---|
| 4,882,353 | 11/1989 | Niewohner et al. | 514/456 |
| 5,082,858 | 1/1992 | Garcia et al. | 514/456 |
| 5,151,442 | 9/1992 | Garcia et al. | 514/456 |

FOREIGN PATENT DOCUMENTS

| | | |
|---|---|---|
| 0 315 009 | 5/1989 | European Pat. Off. . |
| 0370 901 A1 | 5/1990 | European Pat. Off. . |
| 0370 901 B2 | 5/1990 | European Pat. Off. . |
| 0 389 861 A1 | 10/1990 | European Pat. Off. . |
| 0 389 861 B1 | 10/1990 | European Pat. Off. . |
| 0 655 448 A1 | 5/1995 | European Pat. Off. . |
| 0 807 629 A1 | 11/1997 | European Pat. Off. . |
| 1-294677 | 11/1989 | Japan . |

OTHER PUBLICATIONS

E. Lohrmann, et al. "A new class of inhibitors of cAMP–mediated Cl–secretion in rabbit colon, acting by the reduction of cAMP–activated K+ conductance", Pflugers Arch–Eur J Physiol, pp. 517–530 (1995).

R.M. Soll et al., "N–Sulfonamides of Benzopyran–Related Potassium Channel Openers: Conversion of Glyburide Insensitive Smooth Muscle Relaxants to Potent Smooth Muscle Contractors", Bioorganic & Medicinal Chemistry Letters, vol. 4, No. 5, pp. 769–773, (1994).

*Primary Examiner*—Robert W. Ramsuer
*Attorney, Agent, or Firm*—Finnegan, Henderson, Farabow, Garrett & Dunner, L.L.P.

[57] ABSTRACT

Compounds of formula I

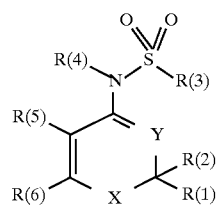

having the meanings indicated in the claims are outstandingly active substances for the production of medicaments for the prophylaxis and therapy of cardiovascular disorders, in particular arrhythmias; for the treatment of ulcers of the gastrointestinal region; or for the treatment of diarrheal illnesses.

20 Claims, No Drawings

SULFONAMIDE-SUBSTITUTED COMPOUNDS, PROCESSES FOR THEIR PREPARATION, THEIR USE AS A MEDICAMENT OR DIAGNOSTIC, AND PHARMACEUTICAL PREPARATION COMPRISING THEM

BACKGROUND OF THE INVENTION

The invention relates to compounds of formula I

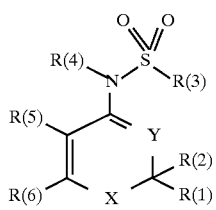

in which X, Y, R(1), R(2), R(3), R(4), R(5) and R(6) have the meanings indicated, their preparation and use, in particular as pharmaceuticals. The compounds affect the potassium channel opened by cyclic adenosine monophosphate (cAMP) or the $I_{K_s}$ channel and are outstandingly suitable as pharmacentically active compounds, for example for the prophylaxis and therapy of cardiovascular disorders, in particular arrhythmias, or for the treatment of ulcers of the gastrointestinal region or diarrheal illnesses.

In recent years in the field of pharmaceutical chemistry, the 4-acylaminochroman derivative class has been studied, and a few corresponding chromene derivatives have also been described. The most prominent representative of this class is cromakalim of formula A, and an example of the corresponding chromene is the compound of formula B (J. Chem. Soc. Perkin Trans. 1, 1991, 63–70).

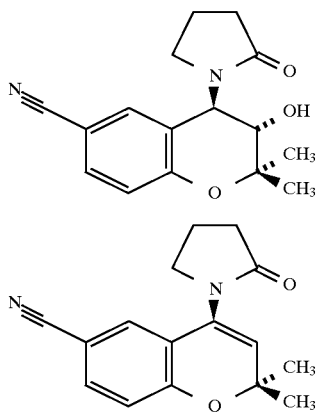

Cromakalim and other related 4-acylaminochroman derivatives are compounds which have a relaxant activity on smooth muscular organs. Thus, they are useful for lowering raised blood pressure as a result of vascular muscle relaxation and in the treatment of asthma as a result of the relaxation of the smooth musculature of the lungs. It is common to all these preparations that they act at the cellular level of smooth muscle cells and cause an opening of specific ATP-sensitive K$^+$ channels of these cells. This increase in the negative charge in the cell (hyperpolarization) induced by the efflux of K$^+$ ions counteracts via secondary mechanisms the increase in intracellular Ca$^{2+}$ concentration which leads to cell activation and which, in turn, leads to muscle contraction.

SUMMARY OF THE INVENTION

The compounds of formula I according to the invention differ structurally from these acylamino derivatives, inter alia by the replacement of the acylamino group with a sulfonylamino function. While cromakalim of formula A and the chromene derivative of formula B and analogous acylamino compounds act as openers of ATP-sensitive K$^+$ channels, the compounds of formula I according to the invention having the sulfonylamino structure do not show any opening activity on this K$^+$ (ATP) channel, but surprisingly show a strong and specific blocking (closing) activity on a K$^+$ channel which is opened by cyclic adenosine monophosphate (cAMP) and which differs fundamentally from the K$^+$ (ATP) channel mentioned. More recent investigations show that this K$^+$ (cAMP) channel identified in colonic tissue is very similar, perhaps even identical, to the $I_{K_s}$ channel identified in cardiac muscle. In fact, the compounds of formula I according to the invention show a strong blocking activity on the $I_{K_s}$ channel in guinea-pig cardiomyocytes as well as on the $I_{sK}$ channel expressed in *Xenopus oocytes*. As a result of this blockage of the K$^+$ (cAMP) channel and of the $I_{Kks}$ channel, the compounds according to the invention have pharmacological activities of high therapeutic utility in the living body.

Compounds with 4-sulfonylaminochroman structure are described in the literature, but, like the cromakalim or acylaminochroman derivatives, the compounds of the prior art differ from the compounds of formula I according to the invention in terms of biological activity. EP-A-315 009 describes chroman derivatives with a 4-phenylsulfonylamino structure having antithrombotic and antiallergic properties. EP-A-389 861 and JP 01294677 describe 3-hydroxychroman or chromene derivatives with a cyclic 4-sulfonylamino group according to formula C, which should act as antihypertensives via activation of the K$^+$ (ATP) channel.

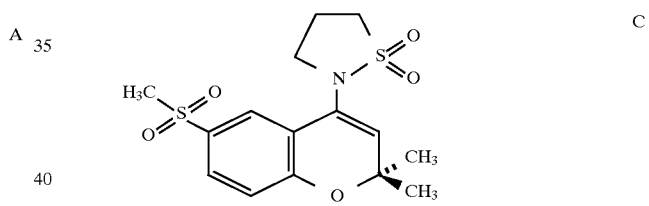

P-A-370 901 discloses 3-hydroxychroman or chromene derivatives with a 4-sulfonylamino group, where the remaining valency of the N atom carries a hydrogen atom, which have CNS activities. Further 4-sulfonylaminochroman derivatives are described in "N-sulfonamides of benzopyran-related potassium channel openers: conversion of glyburyde insensitive smooth muscle relaxants to potent smooth muscle contractors," Bioorg. Med. Chem. Lett. 4 (1994), 769–773.

DETAILED DESCRIPTION OF THE INVENTION

The present invention relates to compounds of formula I

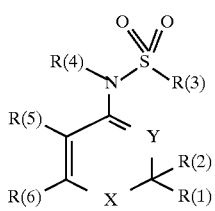

in which:
X is —O—, —S—, —SO—, —SO$_2$—, —NR(7)-, —CR(8a)R(8b)- or or —CO—; R(7) is hydrogen or —(C$_a$H$_{2a}$)—R(9), where a CH$_2$ group of the group C$_a$H$_{2a}$ can be replaced by —O—, —CH=CH—, —C≡C—, —CO—, —CO—O—, —O—CO—, —S—, —SO—, —SO$_2$—, NR(10)- or —CONR(10)-;

R(10) is hydrogen or alkyl having 1, 2 or 3 carbon atoms;

a is zero, 1, 2, 3, 4, 5, 6, 7 or 8;

R(9) is hydrogen, CF$_3$, C$_2$F$_5$, C$_3$F$_7$, cycloalkyl having 3, 4, 5, 6, 7 or 8 carbon atoms, dimethylamino, diethylamino, 1-piperidyl, 1-pyrrolidinyl, 4-morpholinyl, 4-methylpiperazin-1-yl, pyridyl, thienyl, imidazolyl or phenyl, where pyridyl, thienyl, imidazolyl and phenyl are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino; or R(7) and R(1) together are a bond;

R(8a) is hydrogen, CF$_3$, C$_2$F$_5$, C$_3$F$_7$, alkyl having 1, 2, 3, 4, 5 or 6 carbon atoms or phenyl, which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;

R(8b) is hydrogen, alkyl having 1, 2 or 3 carbon atoms, —OR(10), —COOR(10), or —CO—R(10);

R(10) is hydrogen or alkyl having 1, 2 or 3 carbon atoms; or one of the radicals R(8a) or R(8b) together with R(1) is a bond if Y has the meaning of N;

Y is N or CR(11);

R(11) is hydrogen or alkyl having 1, 2 or 3 carbon atoms;

R(1) and R(2) independently of one another are each hydrogen, CF$_3$, C$_2$F$_5$, C$_3$F$_7$, F, Cl, methoxy, alkyl having 1, 2, 3, 4, 5 or 6 carbon atoms or phenyl, which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino; or R(1) and R(2) together are an alkylene chain having 2, 3, 4, 5, 6, 7, 8, 9 or 10 carbon atoms;

R(3) is R(12)-C$_n$—H$_{2n}$—NR(13) or R(12)-C$_n$H$_{2n}$—, where a CH$_2$ group of the group C$_n$H$_{2n}$ can be replaced by —O—, —CO—, —S—, —SO—, —SO$_2$— or —NR(10a);

R(10a) is hydrogen, methyl or ethyl;

R(12) is hydrogen, methyl, cycloalkyl having 3, 4, 5, 6, 7 or 8 carbon atoms, CF$_3$, C$_2$F$_5$ or C$_3$F$_7$;

n is zero, 1, 2, 3, 4, 5, 6, 7, 8, 9 or 10;

R(13) is hydrogen or alkyl having 1, 2, 3, 4, 5 or 6 carbon atoms; or

R(12) and R(13) together are a bond if n is not less than 3; or

R(3) and R(4) together are an alkylene chain having 3, 4, 5, 6, 7 or 8 carbon atoms, where a CH$_2$ group of the alkylene chain can be replaced by —O—, —CO—, —S—, —SO—, —SO$_2$— or —NR(10a)-;

R(10a) is hydrogen, methyl or ethyl;

R(4) is R(14)-C$_r$H$_{2r}$, where a CH$_2$ group of the group C$_r$H$_{2r}$ can be replaced by —O—, —CH=CH—, —C≡C—, —CO—, —CO—O—, —O—CO—, —S—, —SO—, —SO$_2$—, —NR(10b)- or —CONR(10b)-;

R(10b) is hydrogen or alkyl having 1, 2 or 3 carbon atoms;

R(14) is methyl, CF$_3$, C$_2$F$_5$, C$_3$F$_7$, cycloalkyl having 3, 4, 5, 6, 7 or 8 carbon atoms, —OH, —COOH, —NR(23)R(24), 1-piperidyl, 1-pyrrolidinyl, 4-morpholinyl, 4-methylpiperazin-1-yl, pyridyl, thienyl, imidazolyl or phenyl, where pyridyl, thienyl, imidazolyl and phenyl are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;

R(23) and R(24) independently of one another are each hydrogen or alkyl having 1, 2 or 3 carbon atoms; or R(23) and R(24) together are an alkylene chain of 4 or 5 carbon atoms, of which one CH$_2$ group can be replaced by —O—, —S—, —NH—, —N(CH$_3$)— or —N(benzyl)-;

r is zero, 1, 2, 3, 4, 5, 6, 7, 8, 9, 10, 11, 12, 13, 14, 15, 16, 17, 18, 19 or 20;

R(5) and R(6) together are a group
—CR(15)=CR(16)-CR(17)=CR(18)-,
—CR(15)=CR(16)-CR(17)=N—,
—CR(15)=CR(16)-N=CR(18)-,
—CR(15)=N—CR(17)=N—,
—CR(15)=N—N=CR(18)-,
—N=CR(16)-CR(17)=N— or
—S—CR(15)=CR(16)-, where in each case the group may be linked in either direction;

R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —CF$_3$, —C$_2$F$_5$, —C$_3$F$_7$, —N$_3$, —NO$_2$, —Z—C$_s$H$_{2s}$—R(22), thienyl or phenyl, which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —SO$_2$—, —SO$_2$—O—, —SO$_2$NR(10c), —NR(10c)- or —CONR(10c)-;

R(10c) is hydrogen or alkyl having 1, 2 or 3 carbon atoms;

s is zero, 1, 2, 3, 4, 5 or 6;

R(22) is hydrogen, CF$_3$, C$_2$F$_5$, C$_3$F$_7$, cycloalkyl having 3, 4, 5, 6, 7 or 8 carbon atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl, where pyridyl, thienyl, imidazolyl, quinolyl, isoquinolyl and phenyl are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;

R(19) and R(20) independently of one another are each hydrogen or alkyl having 1, 2 or 3 carbon atoms; or R(19) and R(20) together are an alkylene chain of 4 or 5 carbon atoms, of which one CH$_2$ group can be replaced by —O—, —S—, —NH—, —N(CH$_3$)— or —N(benzyl)-;

R(21) is hydrogen or alkyl having 1, 2 or 3 carbon atoms;
but where Y cannot be CR(11) when X is O;
and their physiologically tolerable salts.
Preferred compounds of formula I are those in which:
X is —O—, —S—, —SO—, —SO$_2$—, —NR(7)-, —CR(8a)R(8b)- or —CO—;
R(7) is hydrogen or —(C$_a$H$_{2a}$)—R(9),
where a CH$_2$ group of the group C$_a$H$_{2a}$ can be replaced by —O—, —CH=CH—, —C≡C—, —CO—, —CO—O—, —O—CO—, —S—, —SO—, —SO$_2$—, NR(10)- or —CONR(10)-;
R(10) is hydrogen or alkyl having 1, 2 or 3 carbon atoms;
a is zero, 1, 2, 3, 4, 5, 6, 7 or 8;
R(9) is hydrogen, CF$_3$, C$_2$F$_5$, C$_3$F$_7$, cycloalkyl having 3, 4, 5, 6, 7 or 8 carbon atoms, dimethylamino, diethylamino, 1-piperidyl, 1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or substituted by 1 or 2 substituents, selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(8a) is hydrogen, CF$_3$, C$_2$F$_5$, C$_3$F$_7$, alkyl having 1, 2, 3, 4, 5 or 6 carbon atoms or phenyl,
which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(8b) is hydrogen, alkyl having 1, 2 or 3 carbon atoms, —OR(10), —COOR(10), or —CO—R(10);
R(10) is hydrogen or alkyl having 1, 2 or 3 carbon atoms;
Y is N or CR(11);
R(11) is hydrogen or alkyl having 1, 2 or 3 carbon atoms;
R(1) and R(2) independently of one another are each hydrogen, CF$_3$, C$_2$F$_5$, C$_3$F$_7$, alkyl having 1, 2, 3, 4, 5 or 6 carbon atoms or phenyl,
which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino; or
R(1) and R(2) together are an alkylene chain having 2, 3, 4, 5, 6, 7, 8, 9 or 10 carbon atoms;
R(3) is R(12)-C$_n$—H$_{2n}$—NR(13) or R(12)-C$_n$H$_{2n}$—,
where a CH$_2$ group of the group C$_n$H$_{2n}$ can be replaced by —O—, —CO—, —S—, —SO—, —SO$_2$— or —NR(10a);
R(10a) is hydrogen, methyl or ethyl;
R(12) is hydrogen, methyl, cycloalkyl having 3, 4, 5, 6, 7 or 8 carbon atoms, CF$_3$, C$_2$F$_5$ or C$_3$F$_7$;
n is zero, 1, 2, 3, 4, 5, 6, 7, 8, 9 or 10;
R(13) is hydrogen or alkyl having 1, 2, 3, 4, 5 or 6 carbon atoms; or
R(12) and R(13) together are a bond if n is not less than 3; or
R(3) together with R(4) is an alkylene chain having 3, 4, 5, 6, 7 or 8 carbon atoms,
where a CH$_2$ group of the alkylene chain can be replaced by —O—, —CO—, —S—, —SO—, —SO$_2$— or —NR(10a)-;
R(10a) is hydrogen, methyl or ethyl;

R(4) is R(14)-C$_r$H$_{2r}$,
where a CH$_2$ group of the group C$_r$H$_{2r}$ can be replaced by —O—, —CH=CH—, —C≡C—, —CO—, —CO—O—, —O—CO—, —S—, —SO—, —SO$_2$—, —NR(10b)- or —CONR(10b)-;
R(10b) is hydrogen or alkyl having 1, 2 or 3 carbon atoms;
R(14) is methyl, CF$_3$, C$_2$F$_5$, C$_3$F$_7$, cycloalkyl having 3, 4, 5, 6, 7 or 8 carbon atoms, —OH, —COOH, —NR(23)R(24), 1-piperidyl, 1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(23) and R(24) independently of one another are each hydrogen or alkyl having 1, 2 or 3 carbon atoms; or
R(23) and R(24) together are an alkylene chain of 4 or 5 carbon atoms, of which one CH$_2$ group can be replaced by —O—, —S—, —NH—, —N(CH$_3$)— or —N(benzyl)-;
r is zero, 1, 2, 3, 4, 5, 6, 7, 8, 9, 10, 11, 12, 13, 14, 15, 16, 17, 18, 19 or 20;
R(5) and R(6) together are a group
—CR(15)=CR(16)-CR(17)=CR(18)-,
—CR(15)=CR(16)-CR(17)=N—,
—CR(15)=CR(16)-N=CR(18)-,
—CR(15)=N—CR(17)=N—,
—CR(15)=N—N=CR(18)-,
—N=CR(16)-CR(17)=N— or
—S—CR(15)=CR(16)-,
where in each case the group may be linked in either direction;
R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —CF$_3$, —C$_2$F$_5$, —C$_3$F$_7$, —N$_3$, —NO$_2$, —Z—C$_s$H$_{2s}$—R(22), thienyl or phenyl,
which is unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
Z is —O—, —CO—, —CO—O—, —O—CO—, —S—, —SO—, —SO$_2$—, —SO$_2$—O—, —SO$_2$NR(10c), —NR(10c)- or —CONR(10c)-; R(10c) is hydrogen or alkyl having 1, 2 or 3 carbon atoms;
s is zero, 1, 2, 3, 4, 5 or 6;
R(22) is hydrogen, CF$_3$, C$_2$F$_5$, C$_3$F$_7$, cycloalkyl having 3, 4, 5, 6, 7 or 8 carbon atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl,
where pyridyl, thienyl, imidazolyl, quinolyl, isoquinolyl and phenyl are unsubstituted or substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(19) and R(20) independently of one another are each hydrogen or alkyl having 1, 2 or 3 carbon atoms; or
R(19) and R(20) together are an alkylene chain of 4 or 5 carbon atoms, of which one CH$_2$ group can be replaced by —O—, —S—, —NH—, —N(CH₃)— or —N(benzyl)-;

R(21) is hydrogen or alkyl having 1, 2 or 3 carbon atoms;

but where Y cannot be CR(11) when X is O;

and their physiologically tolerable salts.

Likewise preferred compounds of formula I are those in which:

X is —NR(7)- or —CR(8a)R(8b)-;

R(7) and R(1) together are a bond;

R(8b) is hydrogen, alkyl having 1, 2 or 3 carbon atoms, —OR(10), —COOR(10), or —CO—R(10);

R(10) is hydrogen or alkyl having 1, 2 or 3 carbon atoms; R(8a) and R(1) together are a bond;

Y is N; or CR(11) if X has the meaning of NR(7);

R(11) is hydrogen or alkyl having 1, 2 or 3 carbon atoms;

R(2) is hydrogen, $CF_3$, $C_2F_5$, $C_3F_7$, F, Cl, methoxy, alkyl having 1, 2, 3, 4, 5 or 6 carbon atoms or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(3) is R(12)-$C_nH_{2n}$—NR(13)- or —R(12)-$C_nH_{2n}$—, where a $CH_2$ group of the group $C_nH_{2n}$ can be replaced by —O—, —CO—, —S—, —SO—, —$SO_2$— or —NR(10a)-;

R(10a) is hydrogen, methyl or ethyl;

R(12) is hydrogen, methyl, cycloalkyl having 3, 4, 5, 6, 7 or 8 carbon atoms, $CF_3$, $C_2F_5$ or $C_3F_7$;

n is zero, 1, 2, 3, 4, 5, 6, 7, 8, 9 or 10;

R(13) is hydrogen or alkyl having 1, 2, 3, 4, 5 or 6 carbon atoms; or

R(12) and R(13) together are a bond if n is not less than 3; or

R(3) and R(4) together are an alkylene chain having 3, 4, 5, 6, 7 or 8 carbon atoms;

R(4) is R(14)-$C_rH_{2r}$, where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(10b)- or CONR(10b)-;

R(10b) is hydrogen or alkyl having 1, 2 or 3 carbon atoms;

R(14) is methyl, $CF_3$, $C_2F_5$, $C_3F_7$, cycloalkyl having 3, 4, 5, 6, 7 or 8 carbon atoms, —OH, —COOH, —NR(23) R(24), 1-piperidyl, 1-pyrrolidinyl, 4-morpholinyl, 4-methylpiperazin-1-yl, pyridyl, thienyl or imidazolyl, where pyridyl, thienyl and imidazolyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(23) and R(24) independently of one another are each hydrogen or alkyl having 1, 2 or 3 carbon atoms; or R(23) and R(24) together are an alkylene chain of 4 or 5 carbon atoms, of which one $CH_2$ group can be replaced by —O—, —S—, —NH—, —N(CH₃)— or —N(benzyl)-;

r is zero, 1, 2, 3, 4, 5, 6, 7, 8, 9, 10, 11, 12, 13, 14, 15, 16, 17, 18, 19 or 20;

R(5) and R(6) together are a group —CR(15)=CR(16)-CR(17)=CR(18)- or —S—CR(15)=CR(16)-, where in each case the group may be linked in either direction;

R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Z—$C_sH_{2s}$—R(22), thienyl or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$—O—, —$SO_2$NR(10c)—, —NR(10c)- or —CONR(10c)-;

R(10c) is hydrogen or alkyl having 1, 2 or 3 carbon atoms;

s is zero, 1, 2, 3, 4, 5 or 6;

R(22) is hydrogen, $CF_3$, $C_2F_5$, $C_3F_7$, cycloalkyl having 3, 4, 5, 6, 7 or 8 carbon atoms, —NR(19)R(20), —COOR (21), 1-piperidyl, 1-pyrrolidinyl, 4-morpholinyl, 4-methylpiperazin-1-yl, pyridyl, thienyl, imidazolyl, quinolyl, isoquinolyl or phenyl, where pyridyl, thienyl, imidazolyl, quinolyl, isoquinolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(19) and R(20) independently of one another are each hydrogen or alkyl having 1, 2 or 3 carbon atoms; or R(19) and R(20) together are an alkylene chain of 4 or 5 carbon atoms, of which one $CH_2$ group can be replaced by —O—, —S—, —NH—, —N(CH₃)— or —N(benzyl)-;

R(21) is hydrogen or alkyl having 1, 2 or 3 carbon atoms;

and their physiologically tolerable salts.

Particularly preferred compounds of formula I are those in which:

X is —O—, —S—, —SO—, —$SO_2$—, —NR(7)-, —CR (8a)R(8b)- or —CO—;

R(7) is hydrogen or —($C_aH_{2a}$)—R(9), where a $CH_2$ group of the group $C_aH_{2a}$ can be replaced by —O—, —CH=CH—, —C≡C—, —CO—, —CO—O—, —O—CO—, —S—, —SO—, —$SO_2$—, $_{NR(}$10)- or —CONR(10)-;

R(10) is hydrogen or alkyl having 1, 2 or 3 carbon atoms;

a is zero, 1, 2, 3, 4, 5, 6, 7 or 8;

R(9) is hydrogen, $CF_3$, $C_2F_5$, $C_3F_7$, cycloalkyl having 3, 4, 5, 6, 7 or 8 carbon atoms, dimethylamino, diethylamino, 1-piperidyl, 1-pyrrolidinyl, 4-morpholinyl, 4-methylpiperazin-1-yl, pyridyl, thienyl, imidazolyl or phenyl, where pyridyl, thienyl, imidazolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(8a) is hydrogen, $CF_3$, $C_2F_5$, $C_3F_7$, alkyl having 1, 2, 3, 4, 5 or 6 carbon atoms or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(8b) is hydrogen alkyl having 1, 2 or 3 carbon atoms, —OR(10), —COOR(10), or —CO—R(10);

R(10) is hydrogen or alkyl having 1, 2 or 3 carbon atoms;

Y is N or CR(11);
R(11) is hydrogen or alkyl having 1, 2 or 3 carbon atoms;

R(1) and R(2) independently of one another are hydrogen, $CF_3$, $C_2F_5$, $C_3F_7$, alkyl having 1, 2, 3, 4, 5 or 6 carbon atoms or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino; or R(1) and R(2) together are an alkylene chain having 2, 3, 4, 5, 6, 7, 8, 9 or 10 carbon atoms;

R(3) is $R(12)\text{-}C_n\text{---}H_{2n}\text{---}NR(13)$ or $R(12)\text{-}C_nH_{2n}\text{---}$,
where a $CH_2$ group of the group $C_nH_{2n}$ can be replaced by —O—, —CO—, —S—, —SO—, —$SO_2$— or —NR(10a);
R(10a) is hydrogen, methyl or ethyl;
R(12) is hydrogen, methyl, cycloalkyl having 3, 4, 5, 6, 7 or 8 carbon atoms, $CF_3$, —$C_2F_5$ or $C_3F_7$;
n is zero, 1, 2, 3, 4, 5, 6, 7, 8, 9 or 10;
R(13) is hydrogen or alkyl having 1, 2, 3, 4, 5 or 6 carbon atoms; or
R(12) and R(13) together are a bond if n is not less than 3; or R(3) and R(4) together are an alkylene chain having 3, 4, 5, 6, 7 or 8 carbon atoms,
where a $CH_2$ group of the alkylene chain can be replaced by —O—, —CO—, —S—, —SO—, —$SO_2$— or —NR(10a)-;
R(10a) is hydrogen, methyl or ethyl;

R(4) is $R(14)\text{-}C_rH_{2r}$,
where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(10)- or —CONR(10b)-;
R(10b) is hydrogen or alkyl having 1, 2 or 3 carbon atoms;
R(14) is methyl, $CF_3$, $C_2F_5$, $C_3F_7$, cycloalkyl having 3, 4, 5, 6, 7 or 8 carbon atoms, —OH, —COOH, —NR(23)R(24), 1-piperidyl, 1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(23) and R(24) independently of one another are each hydrogen or alkyl having 1, 2 or 3 carbon atoms; or
R(23) and R(24) together are an alkylene chain of 4 or 5 carbon atoms, of which one $CH_2$ group can be replaced by —O—, —S—, —NH—, —N($CH_3$)— or —N(benzyl)-;
r is zero, 1, 2, 3, 4, 5, 6, 7, 8, 9, 10, 11, 12, 13, 14, 15, 16, 17, 18, 19 or 20;

R(5) and R(6) together are a group —CR(15)=CR(16)-CR(17)=CR(18)-;
R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Z—$C_sH_{2s}$—R(22), thienyl or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$—O—, —$SO_2$NR(10c), —NR(10c)- or —CONR(10c)-;
R(10c) is hydrogen or alkyl having 1, 2 or 3 carbon atoms;
s is zero, 1, 2, 3, 4, 5 or 6;
R(22) is hydrogen, $CF_3$, $C_2F_5$, $C_3F_7$, cycloalkyl having 3, 4, 5, 6, 7 or 8 carbon atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl,
where pyridyl, thienyl, imidazolyl, quinolyl, isoquinolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(19) and R(20) independently of one another are each hydrogen or alkyl having 1, 2 or 3 carbon atoms; or
R(19) and R(20) together are an alkylene chain of 4 or 5 carbon atoms, of which one $CH_2$ group can be replaced by —O—, —S—, —NH—, —N($CH_3$)— or —N(benzyl)-;
R(21) is hydrogen or alkyl having 1, 2 or 3 carbon atoms;
but where Y cannot be CR(11) when X is O;
and their physiologically tolerable salts.

Very particularly preferred compounds of formula I are those in which:

X is —O—, —S—, —SO—, —$SO_2$—, —NR(7)- or —CR(8a)R(8b)-;
R(7) is hydrogen or —($C_aH_{2a}$)—R(9),
where a $CH_2$ group of the group $C_aH_{2a}$ can be replaced by —O—, —CO—, —CO—O—, —$SO_2$— or NR(10)-;
R(10) is hydrogen or alkyl having 1 or 2 carbon atoms;
a is zero, 1, 2, 3 or 4;
R(9) is hydrogen, $CF_3$, cycloalkyl having 5 or 6 carbon atoms, pyridyl, thienyl, imidazolyl or phenyl,
where pyridyl, thienyl, imidazolyl and phenyl are unsubstituted or substituted by 1 or 2 substituents, selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(8a) is hydrogen, $CF_3$, alkyl having 1, 2, 3 or 4 carbon atoms or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(8b) is hydrogen or alkyl having 1, 2 or 3 carbon atoms;
Y is N or CR(11);
R(11) is hydrogen or alkyl having 1, 2 or 3 carbon atoms;
R(1) and R(2) independently of one another are each $CF_3$, alkyl having 1, 2, 3 or 4 carbon atoms or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino; or R(1) and R(2) together are an alkylene chain having 2, 3, 4, 5 or 6 carbon atoms;

R(3) is R(12)-$C_nH_{2n}$—NR(13) or R(12)-$C_nH_{2n}$—;
R(12) is methyl or $CF_3$;
n is zero, 1, 2, 3, 4 or 5;
R(13) is hydrogen or alkyl having 1, 2, 3 or 4 carbon atoms; or R(3) and R(4) together are an alkylene chain having 3 or 4 carbon atoms,
where a $CH_2$ group of the alkylene chain can be replaced by —CO—;

R(4) is R(14)-$C_rH_{2r}$,
where a $CH_2$ group of the group $C_rH_{2r}$ can be replaced by —O—, —CO—, —CO—O—, —O—CO—, —S—, —SO—, —$SO_2$—, —NR(10b)- or —CONR(10b)-;
R(10b) is hydrogen or alkyl having 1 or 2 carbon atoms;

R(14) is methyl, $CF_3$, cycloalkyl having 3, 4, 5, 6 or 7 carbon atoms, —OH, —COOH, —NR(23)R(24), 1-piperidyl, 1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(23) and R(24) independently of one another are each hydrogen or alkyl having 1 or 2 carbon atoms; or
R(23) and R(24) together are an alkylene chain of 4 or 5 carbon atoms, of which one $CH_2$ group can be replaced by —O—, —S—, —NH—, —$N(CH_3)$— or —N(benzyl)-;
r is zero, 1, 2, 3, 4, 5, 6, 7, 8, 9 or 10;

R(5) and R(6) together are a group —CR(15)=CR(16)-CR(17)=CR(18)-;

R(15), R(16), R(17) and R(18) independently of one another are each hydrogen, F, Cl, alkyl having 1, 2 or 3 carbon atoms, —CN, —$CF_3$, —$NO_2$, —Z—$C_sH_{2s}$—R(22), thienyl or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$—O—, —$SO_2$NR(10c), —NR(10c)- or —CONR(10c)-;
R(10c) is hydrogen or alkyl having 1 or 2 carbon atoms;
s is zero, 1, 2, 3 or 4;

R(22) is hydrogen, $CF_3$, cycloalkyl having 5 or 6 carbon atoms, —NR(19)R(20), —COOR(21), pyridyl, thienyl, imidazolyl, quinolyl, isoquinolyl or phenyl,
where pyridyl, thienyl, imidazolyl, quinolyl, isoquinolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(19) and R(20) independently of one another are each hydrogen or alkyl having 1 or 2 carbon atoms; or R(19) and R(20) together are an alkylene chain of 4 or 5 carbon atoms, of which one $CH_2$ group can be replaced by —O—, —S—, —NH— or —$N(CH_3)$—;

R(21) is hydrogen or alkyl having 1 or 2 carbon atoms; but where Y cannot be CR(11) when X is O;

and their physiologically tolerable salts.

Specifically preferred compounds of formula I are those in which:

X is —CR(8a)R(8b)-;
R(8a) is hydrogen;
R(8b) is hydrogen;

Y is CR(11);
R(11) is hydrogen;

R(1) and R(2) independently of one another are each alkyl having 1, 2 or 3 carbon atoms; or R(1) and R(2) together are an alkylene chain having 4 or 5 carbon atoms;

R(3) is R(12)-$C_nH_{2n}$—;
R(12) is methyl;
n is zero, 1 or b 2;

R(4) is R(14)-$C_rH_{2r}$,
where a $CH_2$ group of the group $C_rH_{2r}$ can be replaced by —O—, —CO—, —CO—O—, —O—CO—, —NR(10b)- or —CONR(10b)-;
R(10b) is hydrogen or alkyl having 1 or 2 carbon atoms;

R(14) is methyl, $CF_3$, cycloalkyl having 3, 4, 5 or 6 carbon atoms, —NR(23)R(24), 1-piperidyl, 1-pyrrolidinyl, 4-morpholinyl, pyridyl, thienyl, imidazolyl or phenyl,
where pyridyl, thienyl, imidazolyl and phenyl are unsubstituted or substituted by 1 or 2 substituents selected from the group consisting of F, Cl, $CF_3$, OH, methyl, methoxy, sulfamoyl and methylsulfonyl;
R(23) and R(24) independently of one another are each hydrogen or alkyl having 1 or 2 carbon atoms;
r is zero, 1, 2, 3, 4, 5, 6, 7 or 8;

R(5) and R(6) together are a group —CR(15)=CR(16)-CR(17)=CR(18)-;

R(15), R(16), R(17) and R(18) independently of one another are each hydrogen, F, Cl, alkyl having 1 or 2 carbon atoms, —CN, —$CF_3$, —$NO_2$, —Z—$C_sH_{2s}$—R(22) or phenyl,
which is unsubstituted or substituted by 1 or 2 substituents selected from the group consisting of F, Cl, $CF_3$, OH, methyl, methoxy, sulfamoyl and methylsulfonyl;

Z is —O—,—CO—, —CO—O—, —O—CO—, —$SO_2$—, —$SO_2$—O—, —$SO_2$NR(10c), —NR(10c)- or —CONR(10c)-; R(10c) is hydrogen or methyl;
s is zero, 1, 2, 3 or 4;

R(22) is hydrogen, $CF_3$, cycloalkyl having 5 or 6 carbon atoms, —NR(19)R(20) or phenyl,
which is unsubstituted or substituted by 1 or 2 substituents selected from the group consisting of F, Cl, $CF_3$, OH, methyl, methoxy, sulfamoyl and methylsulfonyl;

R(19) and R(20) independently of one another are each hydrogen or alkyl having 1 or 2 carbon atoms;

and their physiologically tolerable salts.

Specifically preferred compounds of formula I are also those in which:

X is —O—, —NR(7)- or —CR(8a)R(8b)-;
R(7) is hydrogen or —($C_aH_{2a}$)—R(9);

a is zero, 1, 2, 3 or 4;
R(9) is hydrogen or phenyl,
which is unsubstituted or substituted by 1 or 2 substituents, selected from the group consisting of F, Cl, $CF_3$, methyl, methoxy, sulfamoyl and methylsulfonyl;
R(8a) is hydrogen;
R(8b) is hydrogen;
Y is N;
R(1) and R(2) independently of one another are each alkyl having 1, 2 or 3 carbon atoms; or
R(1) and R(2) together are an alkylene chain having 4 or 5 carbon atoms;
R(3) is R(12)-$C_nH_{2n}$—;
R(12) is methyl;
n is zero, 1 or 2;
R(4) is R(14)-$C_rH_{2r}$,
where a $CH_2$ group of the group $C_rH_{2r}$ can be replaced by —O—, —CO—, —CO—O—, —O—CO—, —NR(10)- or —CONR(10b)-;
R(10b) is hydrogen or alkyl having 1 or 2 carbon atoms;
R(14) is methyl, $CF_3$, cycloalkyl having 3, 4, 5 or 6 carbon atoms, —NR(23)R(24), 1-piperidyl, 1-pyrrolidinyl, 4-morpholinyl, pyridyl, thienyl, imidazolyl or phenyl,
where pyridyl, thienyl, imidazolyl and phenyl are unsubstituted or substituted by 1 or 2 substituents selected from the group consisting of F, Cl, $CF_3$, OH, methyl, methoxy, sulfamoyl and methylsulfonyl;
R(23) and R(24) independently of one another are each hydrogen or alkyl having 1 or 2 carbon atoms;
r is zero, 1, 2, 3, 4, 5, 6, 7 or 8;
R(5) and R(6) together are a group —CR(15)=CR(16)-CR(17)=CR(18)-;
R(15), R(16), R(17) and R(18) independently of one another are each hydrogen, F, Cl, alkyl having 1 or 2 carbon atoms, —CN, —$CF_3$, —$NO_2$, —Z—$C_sH_{2s}$—R(22) or phenyl,
which is unsubstituted or substituted by 1 or 2 substituents selected from the group consisting of F, Cl, $CF_3$, OH, methyl, methoxy, sulfamoyl and methylsulfonyl;
Z is —O—, —CO—, —CO—O—, —O—CO—, —$SO_2$—, —$SO_2$—O—, —$SO_2$NR(10c), —NR(10c)- or —CONR(10c)-;
R(10c) is hydrogen or methyl;
s is zero, 1, 2, 3 or 4;
R(22) is hydrogen, $CF_3$, cycloalkyl having 5 or 6 carbon atoms, —NR(19)R(20) or phenyl,
which is unsubstituted or substituted by 1 or 2 substituents selected from the group consisting of F, Cl, $CF_3$, OH, methyl, methoxy, sulfamoyl and methylsulfonyl;
R(19) and R(20) independently of one another are each hydrogen or alkyl having 1 or 2 carbon atoms;
and their physiologically tolerable salts.

Specifically preferred compounds of formula I are furthermore those in which:
X is —NR(7)-, —S—, —SO— or —$SO_2$—;
R(7) is hydrogen or —($C_aH_{2a}$)—R($^9$);
a is zero, 1, 2, 3 or 4;
R(9) is hydrogen or phenyl,
which is unsubstituted or substituted by 1 or 2 substituents, selected from the group consisting of F, Cl, $CF_3$, methyl, methoxy, sulfamoyl and methylsulfonyl;
Y is CR(11);
R(11) is hydrogen;
R(1) and R(2) independently of one another are each alkyl having 1, 2 or 3 carbon atoms; or
R(1) and R(2) together are an alkylene chain having 4 or 5 carbon atoms;
R(3) is R(12)-$C_nH_{2n}$—;
R(12) is methyl;
n is zero, 1 or 2;
R(4) is R(14)-$C_rH_{2r}$,
where a $CH_2$ group of the group $C_rH_{2r}$ can be replaced by —O—, —CO—, —CO—O—, —O—CO—, —NR(10b)- or —CONR(10b)-;
R(10b) is hydrogen or alkyl having 1 or 2 carbon atoms;
R(14) is methyl, $CF_3$, cycloalkyl having 3, 4, 5 or 6 carbon atoms, —NR(23)R(24), 1-piperidyl, 1-pyrrolidinyl, 4-morpholinyl, pyridyl, thienyl, imidazolyl or phenyl,
where pyridyl, thienyl, imidazolyl and phenyl are unsubstituted or substituted by 1 or 2 substituents selected from the group consisting of F, Cl, $CF_3$, OH, methyl, methoxy, sulfamoyl and methylsulfonyl;
R(23) and R(24) independently of one another are each hydrogen or alkyl having 1 or 2 carbon atoms;
r is zero, 1, 2, 3, 4, 5, 6, 7 or 8;
R(5) and R(6) together are a group —CR(15)=CR(16)-CR(17)=CR(18)-;
R(15), R(16), R(17) and R(18) independently of one another are each hydrogen, F, Cl, alkyl having 1 or 2 carbon atoms, —CN, —$CF_3$, —$NO_2$, —Z—$C_sH_{2s}$—R(22) or phenyl,
which is unsubstituted or substituted by 1 or 2 substituents selected from the group consisting of F, Cl, $CF_3$, OH, methyl, methoxy, sulfamoyl and methylsulfonyl;
Z is —O—, —CO—, —CO—O—, —O—CO—, —$SO_2$—, —$SO_2$—O—, —$SO_2$NR(10c), —NR(10c)- or —CONR(10c)-;
R(10c) is hydrogen or methyl;
s is zero, 1, 2, 3 or 4;
R(22) is hydrogen, $CF_3$, cycloalkyl having 5 or 6 carbon atoms, —NR(19)R(20) or phenyl,
which is unsubstituted or substituted by 1 or 2 substituents selected from the group consisting of F, Cl, $CF_3$, OH, methyl, methoxy, sulfamoyl and methylsulfonyl;
R(19) and R(20) independently of one another are each hydrogen or alkyl having 1 or 2 carbon atoms;
and their physiologically tolerable salts.

Particularly preferred compounds of formula I are also those of the type mentioned, in which:
X is —NR(7)-;
R(7) and R(1) together are a bond;
Y is CR(11);
R(11) is hydrogen;
R(2) is hydrogen, $CF_3$, F, Cl, methoxy, or alkyl having 1, 2 or 3 carbon atoms;
R(3) is R(12)-$C_nH_{2n}$—;
R(12) is methyl;
n is zero, 1, or 2;
R(4) is R(14)-$C_rH_{2r}$,
where a $CH_2$ group of the group $C_rH_{2r}$ can be replaced by —O—, —CO—, —CO—O—, —O—CO—, —NR(10b)- or —CONR(10b)-;

R(10b) is hydrogen or alkyl having 1, 2 or 3 carbon atoms;

R(14) is methyl, $CF_3$, $-NR(23)R(24)$, 1-piperidyl, 1-pyrrolidinyl, 4-morpholinyl, 4-methylpiperazin-1-yl, pyridyl, thienyl or imidazolyl, where pyridyl, thienyl and imidazolyl are unsubstituted or substituted by 1 or 2 substituents selected from the group consisting of F, Cl, $CF_3$, OH, methyl, methoxy, dimethylamino, sulfamoyl and methylsulfonyl;

R(23) and R(24) independently of one another are each hydrogen or alkyl having 1, 2 or 3 carbon atoms;

r is zero, 1, 2, 3, 4, 5, 6, 7 or 8;

R(5) and R(6) together are a group $-CR(15)=CR(16)-CR(17)=CR(18)-$;

R(15), R(16), R(17) and R(18) independently of one another are each hydrogen, F, Cl, Br, I, alkyl having 1, 2 or 3 carbon atoms, $-CN$, $-CF_3$, $-NO_2$, $-Z-C_sH_{2s}-R(22)$, thienyl or phenyl, which is unsubstituted or substituted by 1 or 2 substituents selected from the group consisting of F, Cl, $CF_3$, OH, methyl, methoxy, sulfamoyl and methylsulfonyl;

Z is $-O-$, $-CO-$, $-CO-O-$, $-O-CO-$, $-SO_2-$, $-SO_2-O-$, $-SO_2NR(10c)$, $-NR(10c)-$ or $-CONR(10c)-$;

R(10c) is hydrogen or methyl;

s is zero, 1, 2, 3 or 4;

R(22) is hydrogen, $CF_3$, cycloalkyl having 5 or 6 carbon atoms, $-NR(19)R(20)$ or phenyl, which is unsubstituted or substituted by 1 or 2 substituents selected from the group consisting of F, Cl, $CF_3$, OH, methyl, methoxy, dimethylamino, sulfamoyl and methylsulfonyl;

R(19) and R(20) independently of one another are each hydrogen or alkyl having 1 or 2 carbon atoms;

and their physiologically tolerable salts.

In the compounds of formula I, alkyl radicals and alkylene radicals can be straight-chain or branched. This also applies to the alkylene radicals of the formulae $C_aH_{2a}$, $C_nH_{2n}$, $C_rH_{2r}$ and $C_sH_{2s}$. Alkyl radicals and alkylene radicals can also be straight-chain or branched if they are substituted or are contained in other radicals, e.g. in an alkoxy radical or in an alkylmercapto radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, eicosyl. The bivalent radicals derived from these radicals, e.g. methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc. are examples of alkylene radicals. Examples of acyl radicals are formyl, acetyl, propionyl, n-butyryl or isobutyryl.

Monosubstituted phenyl radicals, can be substituted in the 2-, the 3- or the 4-position, or disubstituted in the 2,3-, 2,4-, 2,5-, 2,6-, 3,4-, or 3,5-position. Thienyl radicals can be bonded in the 2- or the 3-position, pyridyl radicals in the 2-, 3- or 4-position, and imidazolyl radicals in the 1-, 2-, 4- or 5-position. In the case of disubstitution of a radical, the substituents can be identical or different.

If the radicals R(1) and R(2) together are an alkylene chain, these radicals together with the carbon atom carrying them form a ring which jointly has a carbon atom with the 6-membered ring in formula I; a spiro compound is thus present. If R(1) and one of the radicals R(7), R(8a) or R(8b) together are a bond, a double bond lies between the groups X and CR(1)R(2), such that the 6-membered ring is aromatic. If R(12) and R(13) together are a bond, the group $R(12)-C_nH_{2n}-NR(13)-$ is preferably a nitrogen heterocycle bonded via a nitrogen atom. If R(12) and R(13) together are a bond and the group $R(12)-C_nH_{2n}-NR(13)-$ is a nitrogen heterocycle bonded via a nitrogen atom, this nitrogen heterocycle is preferably a 4-membered ring or a larger ring than a 4-membered ring, e.g. a 5-membered, 6-membered or 7-membered ring. The bivalent radicals which represent R(5) and R(6), together with the corresponding carbon atoms of the 6-membered ring of formula I, form a fused aromatic ring, e.g. a benzene, pyridine, pyrimidine, pyrazine, pyridazine or thiophene ring. Both linkage directions are possible in each case for the linking of the joint group in the R(5) and R(6) positions. For example, in the case where R(5) and R(6) together are $-S-CR(15)=CR(16)-$, a thiophene ring is fused onto the 6-membered ring of formula I in which the sulfur can be either in the position of R(6) or in the position of R(5).

If the compounds of formula I contain one or more acidic or basic groups or one or more basic heterocycles, the invention relates also to the corresponding physiologically or toxicologically tolerable salts, in particular the pharmaceutically utilizable salts. Thus, the compounds of formula I which carry acidic groups, e.g. one or more COOH groups, are used, for example, as alkali metal salts, preferably sodium or potassium salts, or as alkaline earth metal salts, e.g. calcium or magnesium salts, or as ammonium salts, e.g. as salts with ammonia organic amines or amino acids. Compounds of formula I which carry one or more basic, i.e. protonatable, groups or contain one or more basic heterocyclic rings, can also be used in the form of their physiologically tolerable acid addition salts with inorganic organic acids, for example as hydrochlorides, phosphates, sulfates, methanesulfonates, acetates, lactates, maleates, fumarates, malates, gluconates, etc. If the compounds of formula I simultaneously contain acidic and basic groups in the molecule, beside the salt forms described, the invention also includes internal salts, so-called betaines. Salts can also be obtained from the compounds of formula I according to customary methods, for example by combination with an acid or base in a solvent or dispersant or alternatively from other salts by anion exchange.

When appropriately substituted, the compounds of formula I can be present in stereoisomeric forms. If the compounds of formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to enantiomers, for example, in enantiomerically pure form, both as levo- and dextrorotatory antipodes, and also in the form of mixtures of the two enantiomers in different ratios or in the form of racemates. If cis/trans isomerism is present, the invention relates both to the cis form and to the trans form and mixtures of these forms. The preparation of individual stereoisomers can be carried out, if desired, by resolution of a mixture according to customary methods or, for example, by stereoselective synthesis. If mobile hydrogen atoms are present, the present invention also comprises all tautomeric forms of the compounds of formula I.

The compounds of formula I can be prepared by different chemical processes to which the invention likewise relates. Thus, for example, a compound of formula I is obtained by:

(a) reacting a compound of formula II

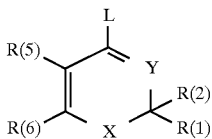

in which R(1), R(2), R(5), R(6), X and Y have the meanings indicated above for formula I and L is a nucleofugic leaving group, in particular F, Cl, Br, I, methanesulfonyloxy or p-toluenesulfonyloxy, in a manner known per se with a sulfonamide or its salt of formula III

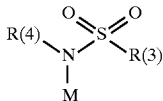

in which R(3) and R(4) have the meanings indicated above for formula I and M is hydrogen or preferably a metal equivalent, particularly preferably lithium, sodium or potassium;

or by (b) reacting a compound of formula IV

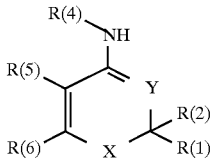

in which R(1), R(2), R(4), R(5), R(6), X and Y have the meanings indicated above, with a sulfonic acid derivative of formula V

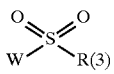

in which R(3) has the meanings indicated above and W is a nucleofugic leaving group, such as, for example, fluorine, bromine, 1-imidazolyl, but in particular chlorine;

or by (c) reacting a compound of formula VI

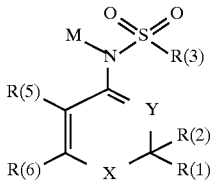

in which R(1), R(2), R(3), R(5), R(6), X, Y and M have the meanings indicated above, in a conventional alkylation reaction with an alkylating agent of formula VII

R(4)-L                                                           VII in which R(4) has the meanings indicated above with the exception of hydrogen and L has the meanings indicated above;

or by (d) carrying out, in a compound of formula I

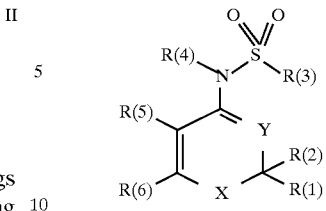

in which R(1) to R(6), X and Y have the meanings indicated above, an electrophilic substitution reaction in at least one of the positions R(15), R(16), R(17), or R(18) of the ring system R(5)–R(6) when this position is hydrogen.

Procedure (a) corresponds to the nucleophilic substitution of a leaving group in a reactive bicyclic system of formula II by a sulfonamide or one of its salts of formula II. Because of the higher nucleophilicity and higher reactivity of a sulfonamide salt, it is advantageous, when using a free sulfonamide (formula III, M=H), to generate a sulfonamide salt (formula III, M=metal cation) by the addition of a base. If a free sulfonamide (formula III, M=H) is employed, deprotonation of the sulfonamide to the salt form can be carried out in situ. Preferably, those bases are used which are not alkylated or only slightly alkylated themselves, such as sodium carbonate, potassium carbonate, sterically strongly hindered amines, e.g. dicyclohexylamine, N,N-dicyclohexylethylamine, or other strong nitrogen bases with low nucleophilicity, for example DBU (diazabicycloundecene), N,N',N'''-triisopropylguanidine, etc. However, it is also possible to employ other customarily used bases for the reaction, such as potassium tert-butoxide, sodium methoxide, alkali metal hydrogen-carbonates, alkali metal hydroxides, such as, for example LiOH, NaOH or KOH, or alkaline earth metal hydroxides, such as, for example, $Ca(OH)_2$.

The reaction of procedure (a) is preferably carried out in a solvent, particularly preferably in a polar organic solvent such as, for example, dimethylformamide (DMF), dimethylacetamide (DMA), dimethyl sulfoxide (DMSO), tetramethylurea (TMU), hexamethylphosphoramide (HMPT), tetrahydrofuran (THF), dimethoxyethane (DME) or other ethers, or, for example, alternatively in a hydrocarbon such as toluene or in a halogenated hydrocarbon such as chloroform or methylene chloride, etc. However, the reaction can also be carried out in polar protic solvents, such as, for example, in water, methanol, ethanol, isopropanol, ethylene glycol or its oligomers or their corresponding hemiethers or ethers. The reaction can also be carried out in mixtures of these solvents. The reaction can equally be carried out, however, entirely without solvent. The reaction is preferably carried out in a temperature range from −10° to +140° C., particularly preferably in the range from 20° to 100° C. Favorably, procedure (a) can also be carried out under the conditions of a phase-transfer catalysis.

The compounds of formula II are obtained by methods known in the literature, for example from the corresponding 4-oxo compounds of formula X

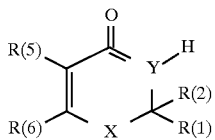

in which R(1), R(2), R(5), R(6), X and Y have the meanings indicated above, or from their tautomeric form (formula II, L=—OH), by the action of an inorganic acid halide, such as, for example, POCl$_3$, PCl$_3$, PCl$_5$, SOCl$_2$, SOBr$_2$, COCl$_2$ or mixtures thereof. Frequently, the use of catalytically acting additives, such as DMF when using SOCl$_2$ or N,N-dimethylaniline when using POCl$_3$, has proven suitable. Advantageously, the reaction is carried out in a solvent which is sufficiently inert to these halogenating energy-rich reagents, such as, for example, in toluene or a halogenated hydrocarbon, such as, for example, in chloroform, methylene chloride or in one of the liquid halogenating agents themselves, preferably in POCl$_3$.

Procedure (b) describes the reaction, which is known per se and frequently used, of a reactive sulfonyl compound of formula V, in particular of a chlorosulfonyl compound (W=Cl), with an amino derivative of formula IV to give the corresponding sulfonamide derivative of formula I. In principle, the reaction can be carried out without solvents, but reactions of this type are in most cases carried out using a solvent.

The reaction is preferably carried out using a polar solvent, preferably in the presence of a base which can advantageously be used as a solvent itself, e.g. triethylamine or in particular pyridine or its homologs. Solvents likewise used are, for example, water, aliphatic alcohols, e.g. methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPT. The reaction is in this case carried out at a temperature from 0° to 160° C., preferably from 20° to 100° C.

The amino derivatives of formula IV are obtained in a manner known per se in the literature, preferably by reaction of the reactive compounds of formula II where R(1), R(2), R(5), R(6), X, Y and L have the meaning indicated, either with ammonia or an amine of formula XI

R(4)-NH$_2$     XI where R(4) has the meaning indicated.

Procedure (c) represents the alkylation reaction known per se of a sulfonamide or of one of its salts of formula VI with an alkylating agent of formula VII. The reaction conditions of procedure (c) are analogous to those described in detail for procedure (a).

The preparation of sulfonamide derivatives of formula VI and precursors thereof has already been described in procedure (b). The preparation of the alkylating agents of formula VII is carried out according to analogous procedures in the literature or as described under procedure (a), preferably from the corresponding hydroxyl compounds (formula VII where L is —OH).

Procedure (d) describes the further chemical conversion of compounds of formula I according to the invention into other compounds of formula I by electrophilic substitution reactions in one or more of the positions of the ring system R(5)–R(6) designated by R(15) to R(18), which in each case are hydrogen.

Preferred electrophilic substitution reactions according to procedure (d) are
1. aromatic nitration to introduce one or more nitro groups which in some or all cases can be reduced to amino groups in subsequent reactions. The amino groups can in turn be converted into other groups in subsequent reactions, for example in a Sandmeyer reaction, e.g. to introduce cyano groups;
2. aromatic halogenation, in particular for the introduction of chlorine, bromine, or iodine;
3. chlorosulfonation, e.g. by the action of chlorosulfonic acid, for the introduction of a chlorosulfonyl group which can be converted into other groups in subsequent reactions, e.g. into a sulfonamide group;
4. the Friedel-Crafts acylation reaction to introduce an acyl radical or a sulfonyl radical by the action of the corresponding acid chloride in the presence of a Lewis acid as a Friedel-Crafts catalyst, preferably in the presence of anhydrous aluminum chloride.

In all procedures, it may be appropriate to protect functional groups in the molecule temporarily in certain reaction steps. Such protective group techniques are familiar to the person of ordinary skill in the art. The choice of a protective group and the methods for their introduction and removal are described in the literature and can be adapted to the individual case, where appropriate, without difficulties.

It has already been said that the compounds of formula I surprisingly have a strong and specific blocking (closing) activity on a K$^+$ channel which is opened by cyclic adenosine monophosphate (cAMP) and fundamentally differs from the well-known K$^+$ (ATP) channel, and that this K$^+$ (cAMP) channel identified in colonic tissue is very similar, perhaps even identical, to the I$_{Ks}$ channel identified in the heart muscle. For the compounds according to the invention, a strong blocking activity was shown on the I$_{Ks}$ channel in guinea-pig cardiomyocytes as well as on the I$_{sK}$ channel expressed in Xenopus oocytes. As a result of this blocking of the K$^+$ (cAMP) channel or of the I$_{Ks}$ channel, the compounds according to the invention display pharmacological activities of high therapeutic utility in the living body and are outstandingly suitable as pharmaceutically active compounds for the therapy and prophylaxis of various syndromes.

The compounds of formula I according to the invention are distinguished as a novel active compound class of potent inhibitors of stimulated gastric acid secretion. The compounds of formula I are thus useful pharmaceutically active compounds for the therapy and prophylaxis of ulcers of the stomach and of the intestinal region, for example of the duodenum. They are likewise suitable, on account of their strong gastric secretion-inhibiting activity, as excellent therapeutics for the therapy and prophylaxis of reflux esophagitis.

The compounds of formula I according to the invention are furthermore distinguished by an antidiarrheal activity and are therefore suitable as pharmaceutically active compounds for the therapy and prophylaxis of diarrheal illnesses.

The compounds of formula I according to the invention are furthermore suitable as pharmaceutically active compounds for the therapy and prophylaxis of cardiovascular disorders. In particular, they can be used for the therapy and prophylaxis of all types of arrhythmias, including atrial, ventricular and supraventricular arrhythmias, especially cardiac arrhythmias which can be eliminated by action potential prolongation. Specifically, they can be used for the therapy and prophylaxis of atrial fibrillation and atrial flutters, and for the therapy and prophylaxis of reentry arrhythmias, as well as for the prevention of sudden heart death as a result of atrial fibrillation.

Although numerous substances having antiarrhythmic activity are already on the market, there is nevertheless no compound which is really satisfactory with respect to activity, range of application and side-effect profile, so that there is furthermore a need for the development of improved antiarrhythmics. The activity of numerous known antiarrhythmics of the so-called class III is based on an increase in the myocardial refractory time by prolongation of the action potential duration. This is essentially determined by the extent of repolarizing K$^+$ streams which flow out of the cell via various K$^+$ channels. Particularly great importance is ascribed in this context to the so-called "delayed rectifier" I$_K$, of which two subtypes exist, a rapidly activated I$_{Kr}$ and a slowly activated I$_{Ks}$. Most known class III antiarrhythmics block I$_{Kr}$ predominantly or exclusively (e.g. dofetilide, d-sotalol). It has been shown, however, that these compounds have an increased proarrhythmic risk at low or normal heart rates, and arrhythmias which are designated as "Torsades de pointes" have been observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging activity of the I$_{Kr}$ blockers is markedly reduced, which is attributed to the fact that under these conditions the I$_{Ks}$ contributes more strongly to the repolarization. For these reasons, the substances according to the invention, which act as I$_{Ks}$ blockers, have significant advantages compared with the known I$_{Kr}$ blockers. In the meantime, it has also been described that a correlation exists between I$_{Ks}$ channel-inhibitory action and the suppression of life-threatening cardiac arrhythmias, such as are elicited, for example, by β-adrenergic hyperstimulation (e.g. T. J. Colatsky, C. H. Follmer and C. F. Starmer, "Channel Specificity in Antiarrhythmic Drug Action; Mechanism of potassium channel block and its role in suppressing and aggravating cardiac arrhythmias," Circulation 82 (1990), 2235–2242; A. E. Busch, K. Malloy, W. J. Groh, M. D. Varnum, J. P. Adelman and J. Maylie, "The novel class III antiarrhythmics NE-10064 and NE-10133 inhibit I$_{sK}$ channels in xenopus oocytes and I$_{Ks}$ in guinea pig cardiac myocytes," Biochem. Biophys. Res. Commun. 202 (1994), 265–270).

Moreover, the compounds of the invention contribute to a marked improvement in cardiac insufficiency, in particular of congestive heart failure, advantageously in combination with contraction-promoting (positively inotropic) active compounds, e.g. phosphodiesterase inhibitors.

In spite of the therapeutically utilizable advantages which can be achieved by a blockade of the I$_{Ks}$, hitherto only very few compounds have been described which inhibit this subtype of the "delayed rectifier". The substance azimilide which is in development admittedly also exhibits blocking activity on the I$_{Ks}$, but mainly blocks the I$_{Kr}$ (selectivity 1:10). WO-A-95/14470 claims the use of benzodiazepines as selective blockers of the I$_{Ks}$. Further I$_{Ks}$ blockers are described in "Specific blockade of slowly activating I$_{sK}$ channels by chromanols . . . ," FEBS Letters 396 (1996), 271–275 and "A new class of inhibitors of cAMP-medicated Cl$^-$ secretion in rabbit colon, acting by the reduction of cAMP-activated K$^+$ conductance," Pflügers Arch.—Eur. J. Physiol. 429 (1995), 517–530. The potency of the 3-hydroxychromanols mentioned, however, is lower than that of the compounds of formula I according to the invention. Moreover, compared with the 3-hydroxychromanols, the compounds of formula I according to the invention have the advantage that the sulfonamide function is not on a chiral carbon atom, so that in contrast to the known compounds, no complicated enantioselective synthesis or resolution is necessary for the production of a homogeneous active compound.

The compounds of formula I according to the invention and their physiologically tolerable salts can thus be used in animals, preferably in mammals, and in particular in humans as pharmaceuticals per se, in mixtures with one another or in the form of pharmaceutical preparations. The present invention also relates to compounds of formula I and their physiologically tolerable salts used as pharmaceuticals in the therapy and prophylaxis of the syndromes mentioned and used in the production of medicaments therefor and of medicaments with K$^+$ channel-blocking activity. Furthermore, the present invention relates to pharmaceutical preparations which, as active constituents contain an effective dose of at least one compound of formula I and/or of one of its physiologically tolerable salts thereof in addition to customary, pharmaceutically innocuous excipients and auxiliaries. The pharmaceutical preparations normally contain 0.1 to 90% by weight of compounds of formula I and/or of their physiologically tolerable salts. The pharmaceutical preparations can be prepared in a manner known per se. For this purpose, the compounds of formula I and/or their physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain compounds of formula I according to the invention and/or their physiologically tolerable salts can be administered orally, parenterally, e.g. intravenously, rectally, by inhalation or topically, the preferred administration being dependent on the individual case, e.g. the particular course of the illness to be treated.

The person of ordinary skill in the art is familiar with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, agents for achieving a depot effect, buffer substances or colorants.

The compounds of formula I can also be combined with other pharmaceutically active compounds to achieve an advantageous therapeutic effect. Thus in the treatment of cardiovascular disorders advantageous combinations with substances having cardiovascular activity are possible. Possible combination components of this type which are advantageous for cardiovascular disorders are, for example, other antiarrhythmics, i.e. class I, class II or class III antiarrhythmics, such as, for example I$_{Kr}$ channel blockers, e.g. dofetilide, or furthermore hypotensive substances such as ACE inhibitors (for example enalapril, captopril, ramipril), angiotensin antagonists, K$^+$ channel activators and also alpha- and beta-receptor blockers, and also sympathomimetic compounds and compounds having adrenergic activity, as well as Na$^+$/H$^+$ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with H$_2$ antagonists (e.g. ranitidine, cimetidine, famotidine, etc.), in particular when used for the treatment of gastrointestinal disorders.

For oral administration, the active compounds of the invention are first mixed with additives suitable for this purpose, such as excipients, stabilizers or inert diluents, and then brought by customary methods into suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case the preparation can be carried out either as dry or as moist granules. Suitable oily excipients or solvents are, for example, vegetable or animal oils, such as sunflower oil or cod-liver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds of the invention are brought into solution, suspension or emulsion, optionally with solubizers, emulsifiers, further auxiliaries, or other substances customary for such administration. The compounds of formula I and their physiologically tolerable salts can also be lyophilized and the lyophilizates obtained can be used, for example, for the production of injection or infusion preparations. Suitable solvents are, for example, water, physiological saline solution or alcohols, e.g. ethanol, propanol, glycerol. In addition, sugar solutions such as glucose or mannitol solutions, or alternatively mixtures of the various solvents mentioned may be used as solvents.

Suitable pharmaceutical formulations for administration in the form of aerosols or sprays are, for example, solutions, suspensions or emulsions of the active compounds of formula I or their physiologically tolerable salts in a pharmaceutically acceptable solvent, such as ethanol or water, or a mixture of such solvents. If required, the formulation may also contain other pharmaceutical auxiliaries such as surfactants, emulsifiers, stabilizers or a propellant gas. Such a preparation customarily contains the active compound of the invention in a concentration from approximately 0.1 to 10%, in particular from approximately 0.3 to 3% by weight.

The dose of the active compound of formula I or of the physiologically tolerable salts thereof to be administered depends on the individual case and, as customary, is to be adapted for an optimum effect to the conditions of the individual case. Thus, it depends on the frequency of administration, on the potency and duration of activity of the compounds employed in each case for therapy or prophylaxis, on the nature and severity of the disease to be treated, on the sex, age, weight and individual responsiveness of the human or animal to be treated, and on whether the therapy is acute or prophylactic. Customarily, the daily dose of a compound of formula I in the case of administration to a patient approximately 75 kg in weight is 0.001 mg/kg of body weight to 100 mg/kg of body weight, preferably 0.01 mg/kg of body weight to 20 mg/kg of body weight. The dose can be administered in the form of one individual dose or divided into several, e.g. two, three or four, individual doses. In particular in the treatment of acute cases of cardiac arrhythmias, for example in an intensive care unit, parenteral administration by injection or infusion, e.g. by an intravenous continuous infusion, can also be advantageous.

The compounds of formula I and their physiologically tolerable salts selectively inhibit $K^+$ (cAMP) channels and $I_{Ks}$ channels. On account of this property, apart from use as pharmaceutically active compounds in human medicine and veterinary medicine, they can also be employed as a scientific tool or as aids for biochemical investigations in which an effect on potassium channels is intended, and also for diagnostic purposes, e.g. in the in vitro diagnosis of cell or tissue samples. They can further be employed, as already mentioned above, as intermediates for the preparation of further pharmaceutically active compounds.

EXAMPLES

List of abbreviations
DMA N,N-dimethylacetamide
m.p. melting point
RT room temperature Example 1

4-(N-Ethylsulfonyl-N-methyl)amino-2-phenylquinazoline

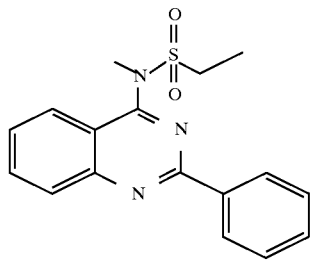

A solution of 0.67 g (5.5 mmol) of ethylsulfonic acid N-methylamide in 10 ml of anhydrous DMA was added dropwise under an argon protective gas atmosphere to a suspension of 0.165 g (5 mmol) of sodium hydride (as an 80% strength dispersion in oil) in 10 ml of anhydrous DMA. The mixture was stirred at room temperature for 4 hours and a suspension of 1.2 g (5 mmol) of 4-chloro-2-phenylquinazoline in 10 ml of anhydrous DMA was then added in portions to this solution and the reaction mixture was stirred at room temperature for 3 days. The solvent was distilled off under reduced pressure, the residue was stirred with water and the microcrystalline substance was filtered off. After washing with water and drying in a stream of air, it was recrystallized from diisopropyl ether. Colorless crystals, m.p. 128°–130° C. Yield: Ig.

Example 2

3-Chloro-1-(N-ethylsulfonyl-N-methyl) aminoisoquinoline

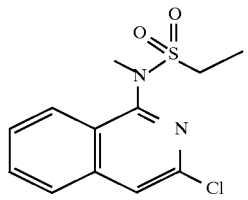

A solution of 0.62 g (5 mmol) of ethylsulfonic acid N-methylamide in 10 ml of anhydrous DMA was added dropwise under an argon protective gas atmosphere to a suspension of 0.22 g (7.6 mmol) of sodium hydride (as an 80% strength dispersion in oil) in 5 ml of anhydrous DMA. The mixture was stirred at room temperature for 1 hour, then 1.09 g (5.5 mmol) of 1,3-dichloroisoquinoline were added, and the mixture was stirred overnight at RT and then for a further 8 h at 80° C. The solvent was distilled off under reduced pressure, the residue was stirred with water and the precipitated solid was filtered off with suction. After purification of the crude product by chromatography on silica gel, 0.34 g of 3-chloro-1-(N-ethylsulfonyl-N-methyl) aminoisoquinoline was obtained; m.p. 116°–118° C.

Example 3

7-Chloro-4-(N-ethylsulfonyl-N-methyl)aminoquinoline

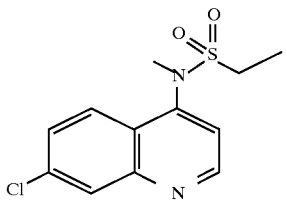

A solution of 0.62 g (5 mmol) of ethylsulfonic acid N-methylamide in 10 ml of anhydrous DMA was added dropwise under an argon protective gas atmosphere to a suspension of 0.22 g (7.6 mmol) of sodium hydride (as an 80% strength dispersion in oil) in 10 ml of anhydrous DMA. The mixture was stirred at room temperature for 1 hour, then 1.09 g (5.5 mmol) of 4,7-dichloroquinoline were added and the mixture was heated at 120° C. for 6 h. The solvent was distilled off under reduced pressure, the residue was stirred with water and the precipitated solid was filtered off with suction. After purification of the crude product by chromatography on silica gel, 0.08 g of 7-chloro-4-(N-ethylsulfonyl-N-methyl)aminoquinoline was obtained; m.p. 273° C.

Example 4

4-(N-Ethylsulfonyl-N-methyl)amino-2,2-dimethyl-2H-benzo[e][1,3]oxazine
a) 4-Chloro-2,2-dimethyl-2H-benzo[e][1,3]oxazine

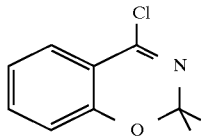

5.3 g (30.0 mmol) of 2,2-dimethyl-2,3-dihydrobenzo[e][1,3]oxazin-4-one, 5.8 ml (45.0 mmol) of N,N-dimethylaniline and 2.2 ml (24 mmol) of phosphorus oxytrichloride were dissolved in 100 ml of absolute toluene and heated to reflux in a water separator for 3 hours. The toluene phase was then decanted off, and washed with 20% strength cold NaOH solution and 2N hydrochloric acid. After drying, the solvent was removed in an oil pump vacuum and 5.3 g of product were obtained as an oil.
b) 4-(N-Ethylsulfonyl-N-methyl)amino-2,2-dimethyl-2H-benzo[e][1,3]oxazine

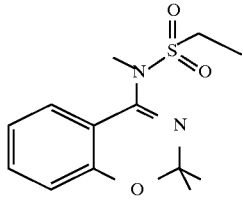

405 mg (3.3 mmol) of ethylsulfonic acid methylamide were added to a suspension of 150 mg (3.6 mmol) of sodium hydride (60% strength) in 7 ml of dimethylacetamide. After 30 min, 600 mg (3 mmol) of 4-chloro-2,2-dimethyl-2H-benzo[e][1,3]oxazine in 6 ml of DMA were added and the mixture was stirred at 80° C. for 24 hours. After diluting with ethyl acetate, the solid was filtered off and the solvent was removed in a high vacuum. After chromatography with heptane/ethyl acetate 4/1, 35 mg of the product were obtained as an oil.

Example 5

4-(N-Ethylsulfonyl-N-methyl)amino-2-trifluoromethylquinoline

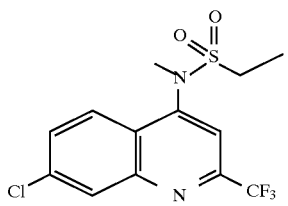

A solution of 0.67 g (5.5 mmol) of ethylsulfonic acid N-methylamide in 10 ml of anhydrous DMA was added dropwise under an argon protective gas atmosphere to a suspension of 0.165 g (5.5 mmol) of sodium hydride (as an 80% strength dispersion in oil) in 10 ml of anhydrous DMA. The mixture was stirred at RT for 4 hours, then a solution of 1.15 g (5.0 mmol) of 4-chloro-2-trifluoromethylquinoline was added and the mixture was stirred for a further 3 days at RT. The solvent was distilled off under reduced pressure, and the residue was treated with water and extracted with ethyl acetate. After purification of the crude product by chromatography on silica gel using ethyl acetate/cyclohexane 1:1, 0.6 g of 4-(N-ethylsulfonyl-N-methyl)amino-2-trifluoromethylquinoline was obtained as a yellowish oil.

Example 6

8-Chloro-4-(N-ethylsufonyl-N-methyl)amino-2-trifluoromethylquinoline

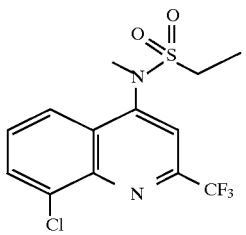

Analogously to Example 5, 0.5 g of 8-chloro-4-(N-ethylsulfonyl-N-methyl)amino-2-trifluoromethylquinoline was obtained as an oil from 1.33 g of 4,8-dichloro-2-trifluoromethylquinoline.

What is claimed is:

1. A compound of formula I

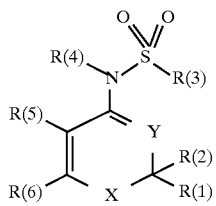

in which:

X is —NR(7)-;

R(7) and R(1) together are a bond;

Y is CR(11);

R(11) is hydrogen or alkyl having 1, 2 or 3 carbon atoms; R(2) is hydrogen, $CF_3$, $C_2F_5$, $C_3F_7$, F, Cl, methoxy, alkyl having 1, 2, 3, 4, 5 or 6 carbon atoms or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(3) is R(12)-$C_n$—$H_{2n}$—NR(13) or R(12)-$C_nH_{2n}$—, where a $CH_2$ group of the group $C_nH_{2n}$ can be replaced by —O—, —CO—, —S—, —SO—, —$SO_2$— or —NR(10a);

R(10a) is hydrogen, methyl or ethyl;

R(12) is hydrogen, methyl, cycloalkyl having 3, 4, 5, 6, 7 or 8 carbon atoms, $CF_3$, $C_2F_5$ or $C_3F_7$;

n is zero, 1, 2, 3, 4, 5, 6, 7, 8, 9 or 10;

R(13) is hydrogen or alkyl having 1, 2, 3, 4, 5 or 6 carbon atoms; or

R(12) and R(13) together are a bond if n is not less than 3; or

R(3) and R(4) together are an alkylene chain having 3, 4, 5, 6, 7 or 8 carbon atoms, where a $CH_2$ group of the alkylene chain can be replaced by —O—, —CO—, —S—, —SO—, —$SO_2$— or —NR(10a)-;

R(10a) is hydrogen, methyl or ethyl;

R(4) is R(14)-$C_rH_{2r}$, where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(10b)- or —CONR(10b)-;

R(10b) is hydrogen or alkyl having 1, 2 or 3 carbon atoms;

R(14) is methyl, $CF_3$, $C_2F_5$, $C_3F_7$, cycloalkyl having 3, 4, 5, 6, 7 or 8 carbon atoms, —OH, —COOH, —NR(23) R(24), 1-piperidyl, 1-pyrrolidinyl, 4-morpholinyl, 4-methylpiperazin-1-yl, pyridyl, thienyl, imidazolyl or phenyl, where pyridyl, thienyl, imidazolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(23) and R(24) independently of one another are each hydrogen or alkyl having 1, 2 or 3 carbon atoms; or R(23) and R(24) together are an alkylene chain of 4 or 5 carbon atoms, of which one $CH_2$ group can be replaced by —O—, —S—, —NH—, —N($CH_3$)— or —N(benzyl)-;

r is zero, 1, 2, 3, 4, 5, 6, 7, 8, 9, 10, 11, 12, 13, 14, 15, 16, 17, 18, 19 or 20;

R(5) and R(6) together are a group —CR(15)=CR(16)-CR(17)=CR(18)-, where the group may be linked in either direction;

R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Z—$C_sH_{2s}$—R(22), thienyl or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$—O—, —$SO_2$NR(10c), —NR(10c)- or —CONR(10c)-;

R(10c) is hydrogen or alkyl having 1, 2 or 3 carbon atoms;

s is zero, 1, 2, 3, 4, 5 or 6;

R(22) is hydrogen, $CF_3$, $C_2F_5$, $C_3F_7$, cycloalkyl having 3, 4, 5, 6, 7 or 8 carbon atoms, —NR(19)R(20), —COOR (21), 1-piperidyl, 1-pyrrolidinyl, 4-morpholinyl, 4-methylpiperazin-1-yl, pyridyl, thienyl, imidazolyl, quinolyl, isoquinolyl or phenyl, where pyridyl, thienyl, imidazolyl, quinolyl, isoquinolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(19) and R(20) independently of one another are each hydrogen or alkyl having 1, 2 or 3 carbon atoms; or R(19) and R(20) together are an alkylene chain of 4 or 5 carbon atoms, of which one $CH_2$ group can be replaced by —O—, —S—, —NH—, —N($CH_3$)— or —N(benzyl)-;

R(21) is hydrogen or alkyl having 1, 2 or 3 carbon atoms; or a physiologically tolerable salt thereof.

2. A compound of the formula I as claimed in claim 1, in which:

X is —NR(7)—;

R(7) and R(1) together are a bond;

Y CR(11);

R(11) is hydrogen or alkyl having 1, 2 or 3 carbon atoms;

R(2) is hydrogen, $CF_3$, $C_2F_5$, $C_3F_7$, F, Cl, methoxy, alkyl having 1, 2, 3, 4, 5 or 6 carbon atoms or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(3) is R(12)-$C_nH_{2n}$—NR(13)- or —R(12)-$C_nH_{2n}$—, where a $CH_2$ group of the group $C_nH_{2n}$ can be replaced by —O—, —CO—, —S—, —SO—, —$SO_2$— or —NR(10a)-;

R(10a) is hydrogen, methyl or ethyl;

R(12) is hydrogen, methyl, cycloalkyl having 3, 4, 5, 6, 7 or 8 carbon atoms, $CF_3$, $C_2F_5$ or $C_3F_7$;

n is zero, 1, 2, 3, 4, 5, 6, 7, 8, 9 or 10;

R(13) is hydrogen or alkyl having 1, 2, 3, 4, 5 or 6 carbon atoms; or

R(12) and R(13) together are a bond if n is not less than 3; or

R(3) and R(4) together are an alkylene chain having 3, 4, 5, 6, 7 or 8 carbon atoms;

R(4) is R(14)-$C_rH_{2r}$,
where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(10)- or CONR(10b)-;

R(10b) is hydrogen or alkyl having 1, 2 or 3 carbon atoms;

R(14) is methyl, $CF_3$, $C_2F_5$, $C_3F_7$, cycloalkyl having 3, 4, 5, 6, 7 or 8 carbon atoms, —OH, —COOH, —NR(23)R(24), 1-piperidyl, 1-pyrrolidinyl, 4-morpholinyl, 4-methylpiperazin-1-yl, pyridyl, thienyl or imidazolyl,
where pyridyl, thienyl and imidazolyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(23) and R(24) independently of one another are each hydrogen or alkyl having 1, 2 or 3 carbon atoms; or R(23) and R(24) together are an alkylene chain of 4 or 5 carbon atoms, of which one $CH_2$ group can be replaced by —O—, —S—, —NH—, —N($CH_3$)— or —N(benzyl)-;

r is zero, 1, 2, 3, 4, 5, 6, 7, 8, 9, 10, 11, 12, 13, 14, 15, 16, 17, 18, 19 or 20;

R(5) and R(6) together are a group —CR(15)=CR(16)-CR(17)-CR(18)-,
where the group may be linked in either direction;

R(15), R(16), R(17) and R(18) independently of one another are each hydrogen, F, Cl, Br, I, alkyl having 1, 2, 3, 4 or 5 carbon atoms, cycloalkyl having 3, 4, 5, 6, 7 or 8 carbon atoms, —CN, —$CF_3$, —$C_2F_5$, —$C_3F_7$, —$N_3$, —$NO_2$, —Z—$C_sH_{2s}$—R(22), thienyl or phenyl, which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$—O—, —$SO_2$NR(10c)- or —CONR(10c)-;

R(10c) is hydrogen or alkyl having 1, 2 or 3 carbon atoms;

s is zero, 1, 2, 3, 4, 5 or 6;

R(22) is hydrogen, $CF_3$, $C_2F_5$, $C_3F_7$, cycloalkyl having 3, 4, 5, 6, 7 or 8 carbon atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl,
where pyridyl, thienyl, imidazolyl, quinolyl, isoquinolyl and phenyl are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(19) and R(20) independently of one another are hydrogen or alkyl having 1, 2 or 3 carbon atoms; or R(19) and R(20) together are an alkylene chain of 4 or 5 carbon atoms, of which one $CH_2$ group can be replaced by —O—, —S—, —NH—, —N($CH_3$)— or —N(benzyl)-;

R(21) is hydrogen or alkyl having 1, 2 or 3 carbon atoms; or a physiologically tolerable salt thereof.

3. A compound of formula I as claimed in claim 2, in which:

X is —NR(7)-;
R(7) and R(1) together are a bond;

Y is CR(11);
R(11) is hydrogen;

R(2) is hydrogen, $CF_3$, F, Cl, methoxy, or alkyl having 1, 2 or 3 carbon atoms;

R(3) is R(12)-$C_nH_{2n}$—;
R(12) is methyl;
n is zero, 1, or 2;

R(4) is R(14)-$C_rH_{2r}$,
where a $CH_2$ group of the group $C_rH_{2r}$ can be replaced by —O—, —CO—, —CO—O—, —O—CO—, —NR(10b)- or —CONR(10b)-;

R(10b) is hydrogen or alkyl having 1, 2 or 3 carbon atoms;

R(14) is methyl, $CF_3$, —NR(23)R(24), 1-piperidyl, 1-pyrrolidinyl, 4-morpholinyl, 4-methylpiperazin-1-yl, pyridyl, thienyl or imidazolyl,
where pyridyl, thienyl and imidazolyl are unsubstituted or substituted by 1 or 2 substituents selected from the group consisting of F, Cl, $CF_3$, OH, methyl, methoxy, dimethylamino, sulfamoyl and methylsulfonyl;

R(23) and R(24) independently of one another are each hydrogen or alkyl having 1, 2 or 3 carbon atoms;

r is zero, 1, 2, 3, 4, 5, 6, 7 or 8;

R(5) and R(6) together are a group —CR(15)=CR(16)-CR(17)=CR(18)-;

R(15), R(16), R(17) and R(18) independently of one another are each hydrogen, F, Cl, Br, I, alkyl having 1, 2 or 3 carbon atoms, —CN, —$CF_3$, —$NO_2$, —Z—$C_sH_{2s}$—R(22), thienyl or phenyl,
which is unsubstituted or substituted by 1 or 2 substituents selected from the group consisting of F, Cl, $CF_3$, OH, methyl, methoxy, sulfamoyl and methylsulfonyl;

Z is —O—, —CO—, —CO—O—, —O—CO—, —$SO_2$—, —$SO_2$—O—, —$SO_2$NR(10c), —NR(10c)- or —CONR(10c)-; R(10c) is hydrogen or methyl;

s is zero, 1, 2, 3 or 4;

R(22) is hydrogen, $CF_3$, cycloalkyl having 5 or 6 carbon atoms, —NR(19)R(20) or phenyl,
which is unsubstituted or substituted by 1 or 2 substituents selected from the group consisting of F, Cl, $CF_3$, OH, methyl, methoxy, dimethylamino, sulfamoyl and methylsulfonyl;

R(19) and R(20) independently of one another are each hydrogen or alkyl having 1 or 2 carbon atoms; or a physiologically tolerable salt thereof.

4. A process for the preparation of a compound of formula I as claimed in claim 1, which comprises
(a) reacting a compound of formula II

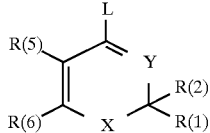

in which R(1), R(2), R(5), R(6), X and Y have the meanings indicated in claim 1 and L is a nucleofugic leaving group, with a sulfonamide or its salt of formula III

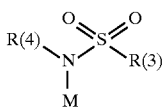

in which R(3) and R(4) have the meanings indicated in claim 1 and M is hydrogen or a metal equivalent;
or by
(b) reacting a compound of formula IV

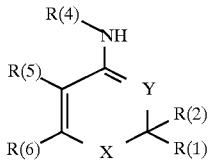

in which R(1), R(2), R(4), R(5), R(6), X and Y have the meanings indicated in claim 1, with a sulfonic acid derivative of formula V

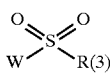

in which R(3) has the meanings indicated in claim 1 and W is a nucleofugic leaving group;
or by
c) reacting a compound of formula VI

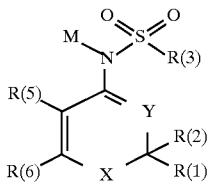

in which R(1), R(2), R(3), R(5), R(6), X, and Y have the meanings indicated in claim 1 and M is hydrogen or a metal ion equivalent, with an alkylating agent of formula VII

in which R(4) has the meanings indicated in claim 1 with the exception of hydrogen, and L is a nucleofugic leaving group;
or by
d) carrying out, in a compound of formula I

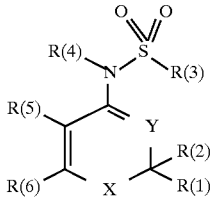

in which R(1) to R(6), X and Y have the meanings indicated in claim 1, an electrophilic substitution reaction in at least one of the positions R(15), R(16), R(17), or R(18) of the ring system R(5)-R(6), when this position is hydrogen.

5. A method as claimed in claim 4, wherein in reaction (a), M is a metal equivalent.

6. A pharmaceutical composition comprising an effective amount of at least one compound of formula I as claimed in claim 1 or of a physiologically tolerable salt thereof; together with a pharmaceutically acceptable excipient, additive, or a mixture of an excipient and additive, and, optionally, one or more other pharmacologically active compounds.

7. A method for the therapy or prophylaxis of a K+ channel-mediated disease which comprises administering to a host in need of said therapy or prophylaxis a therapeutically effective amount of at least one compound of formula I as claimed in claim 1 or a physiologically tolerable salt thereof.

8. A method for the inhibition of gastric acid secretion which comprises administering to a host in need of said inhibition a therapeutically effective amount of at least one compound of formula I as claimed in claim 1 or a physiologically tolerable salt thereof.

9. A method for the therapy or prophylaxis of ulcers of the stomach or intestinal region which comprises administering to a host in need of said therapy or prophylaxis a therapeutically effective amount of at least one compound of formula I as claimed in claim 1 or a physiologically tolerable salt thereof.

10. A method for the therapy or prophylaxis of reflux esophagitis which comprises administering to a host in need of said therapy or prophylaxis a therapeutically effective amount of at least one compound of formula I as claimed in claim 1 or a physiologically tolerable salt thereof.

11. A method for the therapy or prophylaxis of a diarrheal illness which comprises administering to a host in need of said therapy or prophylaxis a therapeutically effective amount of at least one compound of formula I as claimed in claim 1 or a physiologically tolerable salt thereof.

12. A method for the therapy or prophylaxis of arrhythmia which comprises administering to a host in need of said therapy or prophylaxis a therapeutically effective amount of at least one compound of formula I as claimed in claim 1 or a physiologically tolerable salt thereof.

13. A method according to claim 12 wherein the arrhythmia is atrial arrhythmia, ventricular arrhythmia, or supraventricular arrhythmia.

14. A method for the therapy or prophylaxis of cardiac arrhythmia which can be eliminated by action potential prolongation which comprises administering to a host in need of said therapy or prophylaxis a therapeutically effective amount of at least one compound of formula I as claimed in claim 1 or a physiologically tolerable salt thereof.

15. A method for the therapy or prophylaxis of atrial fibrillation or atrial flutters which comprises administering to a host in need of said therapy or prophylaxis a therapeutically effective amount of at least one compound of formula I as claimed claim 1 or a physiologically tolerable salt thereof.

16. A method for the therapy or prophylaxis of reentry arrhythmia which comprises administering to a host in need of said therapy or prophylaxis a therapeutically effective amount of at least one compound of formula I as claimed in claim 1 or a physiologically tolerable salt thereof.

17. A method for the prevention of sudden heart death as a result of ventricular fibrillation which comprises administering to a host in need of said prevention a preventative effective amount of at least one compound of formula I as claimed in claim 1 or a physiologically tolerable salt thereof.

18. A method for the therapy of cardiac insufficiency which comprises administering to a host in need of said therapy a therapeutically effective amount of at least one compound of formula I as claimed in claim 1 or a physiologically tolerable salt thereof.

19. A method as claimed in claim 18 for the therapy of congestive heart failure which comprises administering to a host in need of said therapy a therapeutically effective amount of at least one compound of formula I as claimed claim 1 or a physiologically tolerable salt thereof.

20. A method for blocking a calcium channel which is opened by cyclic adenosine monophosphate (cAMP) which comprises administering to a host in need of said blocking an effective amount of at least one compound of formula I as claimed in claim 1 or a physiologically tolerable salt thereof.

\* \* \* \* \*

UNITED STATES PATENT AND TRADEMARK OFFICE
CERTIFICATE OF CORRECTION

PATENT NO. : 5,856,338
DATED : January 5, 1999
INVENTOR(S) : Brendel et al.

It is certified that error appears in the above-identified patent and that said Letters Patent is hereby corrected as shown below:

Column 1, line 5 and
 *Title Page, Item [54], in the Title, line 5 "PREPARATION"
   should read --PREPARATIONS--.

Claim 2, col. 28, line 46, after "Y", insert --is--.

*Claim 2, col. 29, line 7, "-NR (10)-" should read -- -NR(10b)- --.

Claim 15, col. 32, line 49, after "claimed", insert --in--.

Claim 19, col. 33, line 5, before "claim", insert --in--.

Signed and Sealed this

Sixteenth Day of November, 1999

Attest:

Q. TODD DICKINSON

Attesting Officer

Acting Commissioner of Patents and Trademarks